United States Patent [19]

Konrad et al.

[11] Patent Number: 4,543,425

[45] Date of Patent: Sep. 24, 1985

[54] 1,3-DIAMINO-4-(2',2',2',-TRIFLUOROETHOXY)-BENZENE, METHOD OF PRODUCING THE SAME, AND HAIR COLORING COMPOSITION CONTAINING THE SAME

[75] Inventors: Eugen Konrad, Darmstadt, Fed. Rep. of Germany; Hans J. Braun, Marly; Herbert Mager, Fribourg, both of Switzerland; Friedrich Noser, Bonnefontaine; Max Bracher, Albligen, both of Switzerland

[73] Assignee: Wella AG, Darmstadt, Fed. Rep. of Germany

[21] Appl. No.: 521,165

[22] Filed: Aug. 5, 1983

[30] Foreign Application Priority Data

Aug. 12, 1982 [DE] Fed. Rep. of Germany ....... 3229973

[51] Int. Cl.$^4$ .............................................. C07C 87/60
[52] U.S. Cl. ..................... 564/442; 564/443; 8/406; 8/411
[58] Field of Search ................... 8/411, 406; 564/442, 564/443

[56] References Cited

U.S. PATENT DOCUMENTS 3,929,823  12/1975  Beard et al. ..................... 564/440

OTHER PUBLICATIONS

JACS (1976), vol. 98(18), p. 5663, Bunton et al.

Primary Examiner—Charles F. Warren
Assistant Examiner—Harry B. Shubin
Attorney, Agent, or Firm—Michael J. Striker

[57] ABSTRACT

1,3-diamino-4-(2',2',2'-trifluoroethoxy)-benzene, as well as its acid addition salts, are used as new compounds to serve as coupler substance in hair dyeing compositions and yields with known developer substances 1,4-diaminobenzene and 2,5-diaminobenzylalcohol to stable blue tones without any red fraction. Moreover, the new compounds lead to exceptional black tones and ash tones.

16 Claims, No Drawings

1,3-DIAMINO-4-(2′,2′,2′,-TRIFLUOROETHOXY)-BENZENE, METHOD OF PRODUCING THE SAME, AND HAIR COLORING COMPOSITION CONTAINING THE SAME

BACKGROUND OF THE INVENTION

The invention relates to the general field of dyeing of hair. For dyeing of hair, the so-called oxidative dyes are of preferred interest because of their intense color and very good fastness properties and are obtained by oxidative coupling of a developer component with a coupler component.

Numerous particular demands are put forward with respect to the oxidative dyes used for dyeing human hair. They must be unobjectionable toxicologically and dermatologically and permit one to obtain colorings to the desired intensity. Furthermore, it is necessary to provide a wide range of various coloring shades through the combination of suitable developer components and coupler components. Moreover, the obtainable hair colorings must meet a good fastness to light, permanent waving, acid and rubbing. In any case, these hair colorings must remain stable without the influence of light, chemical agents and rubbing for a period of at least 4–6 weeks. As developer substances, usually 4-aminophenol, 1,4-diaminobenzene as well as its derivatives, 2,5-diaminotoluene and 2,5-diaminoanisole are used. A certain relevance is also attributed to 1,4-diaminobenzene derivatives, 2,5-diaminobenzyl alcohol and 1,4-diamino-2-($\beta$-hydroxyethyl)-benzene.

The preferably used coupler substances are resorcin, 4-chlororesorcin, m-aminophenol, 5-amino-2-methylphenol, 1-naphthol, m-phenylenediamine and its derivatives as for example 2-amino-4-($\beta$-hydroxyethylamino)-anisole or 2,4-diaminophenoxyethanol. Moreover, also 4-hydroxy-1,2-methylenedioxybenzene and 4-($\beta$-hydroxyethylamino)-1,2-methylenedioxybenzene can be used as coupler substances.

The m-pheneylenediamine and its derivatives have gained some importance as so-called blue couplers because of their ability to produce blue tones upon the oxidative coupling with 1,4-diaminobenzene and 1,4-diaminobenzene derivatives. The color character, the stability and also the intensity of the so produced blue tones are determined by the chemical constitution of the used 1,4-diaminobenzene derivatives as well as by the chemical structure of the m-phenylenediamine derivatives. Although very intense blue tones can be produced during the use of known blue couplers like 2,4-diaminoanisole, 2,4-diaminophenetole and 2,4-diaminophenoxyethanol; however, these blue tones show a red fraction. This red fraction is especially undesired for producing mat black tones in combination with the developers 1,4-diaminobenzene or 2,5-diaminobenzene alcohol. It is true that these mat black tones can be produced with m-phenylenediamine, but it is to be noted that the obtained black tones are very unstable and change their color to rust brown after some weeks.

SUMMARY OF THE INVENTION

It is the general object of the present invention to overcome the prior-art disadvantages.

In particular, it is an object of the present invention to provide a new coloring compound as coupler substance for hair dyeing compositions for oxidative dyeing of hair.

Yet another object of the present invention is to provide a new coloring compound as coupler substance which does not have the disadvantages of the m-phenylenediamine and its derivatives and is suitable to meet all proposed requirements in an optimum manner.

A concomitant object of the present invention is to provide a hair dyeing composition as well as a method for dyeing hair on the basis of the new coloring coupling compound.

These objects are met by 1,3-diamino-4-(2′,2′,2′-trifluoroethoxy)-benzene of the general formula I

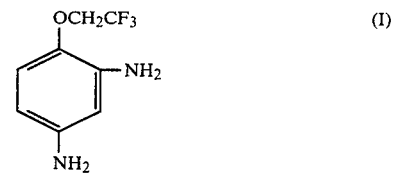

as well as by acid addition salts of this compound obtained with organic or inorganic acids like for example the hydrochloride, the hydrobromide or the sulfate.

The inventive new compounds of the formula I are obtained by heating under reflux 1-chloro-2,4-dinitrobenzene is a solution of sodium in dry 2,2,2-trifluoroethanol for several hours, especially 3 hours. The excess trifluoroethanol is then distilled off, the remaining oil is dissolved in ethanol and the obtained 1,3-dinitro-4-(2′,2′,2′-trifluoroethoxy)-benzene is precipitated under addition of water. The 1,3-dinitro-4-(2′,2′,2′-trifluoroethoxy)-benzene which if necessary may be purified is then hydrated to 1,3-diamino-4-(2′,2′,2′-trifluoroethoxy)-benzene in a manner known per se in the presence of a catalyst, preferably palladium on active carbon.

The acid addition salts of the new compound of formula I can be obtained by reaction with respective organic or inorganic acids.

The new compound according to the invention is a coupler substance which in combination with developer substances known in the field of hair coloring is exceptionally suitable for coloring of hair.

This coupler substance is to be used in the hair coloring compositions either as such or in form of its physiologically compatible salts with inorganic or organic acids, for example as chloride, sulfate, phosphate, acetate, propionate, lactate or citrate.

The inventive coupler substance is usually used in approximately molar amounts relative to the used developer substances. Although the molar use has been proven suitable, it is to be mentioned that there is no disadvantage when the coupler substance is used in a certain excess or certain deficiency. Moreover, it is not necessary to provide the developer components and the coupler components as uniform products, rather the developer component can be a mixture of known developer substances and the coupler component can be a mixture of the compound according to the invention with known coupler substances.

In hair dyeing compositions the new inventive coupler substance is to be contained in a concentration of approximately 0.01 to 4.0% by weight, preferably 0.02 to 2.0% by weight.

Moreover, the hair dyeing compositions can additionally contain known coupler substances, especially 1-naphthol, 4-methoxy-1-naphthol, resorcin, 4-chlororesorcin, 4,6-dichlororesorcin, 2-methylresorcin, m-aminophenol, 5-amino-2-methylphenol, 4-hydroxy- 1,2-methylenedioxybenzene, 4-amino-1,2-methylenedioxybenzene and 4-(β-hydroxyethylamino)-1,2-methylenedioxybenzene. Further suitable coupler substances are for example 2,4-dihydroxyphenolethers such as 2,4-dihydroxyanisole and 2,4-dihydroxyphenoxyethanol.

As known developer substances, especially 1,4-diaminobenzene, 2,5-diaminotoluene, 2,5-diaminoanisole, 2,5-diaminobenzylalcohol, 3-methyl-4-aminophenol, 2-(β-hydroxyethyl)-1,4-diaminobenzene, tetraaminopyrimidine and 4-aminophenol are used as components in the hair dyeing composition according to the invention.

The overall amount of the combination of developer substance and coupler substance used in the described hair dyeing composition should approximately amount to 0.1 to 6.0% by weight, preferably 0.5 to 3.0% by weight.

For obtaining certain coloring shades, in addition also customary direct dye stuffs can be used as for example triphenylmethane dye stuffs as Diamond Fuchsin (C.I. 42 510) and Leather Ruby HF (C.I. 42 520), aromatic nitro dye stuffs such as 2-amino-4, 6-dinitrophenol, 2-nitro-4(β-hydroxyethylamino)-aniline and 2-amino-4-nitrophenol, azo dye stuffs such as Acid Brown 4 (C.I. 14 805) and Acid Blue 135 (C.I. 13 385), anthraquinone dye stuffs such as Disperse Violet 4 (C.I. 61 105), Disperse 1 Blue 1 (C.I. 64 500), Disperse Red 15 (C.I. 60 710), Disperse Violet 1 (C.I. 61 100), or 1,4,5,8-tetraaminoanthraquinone and 1,4-diaminoanthraquinone.

The claimed hair dyeing compositions can further contain self-coupling coloring components, such as for example 2-amino-5-methylphenol, 2-amino-6methylphenol, 2-amino-5-ethoxyphenol or 2-propylamino-5-aminopyridine.

Finally, the hair dyeing compositions can contain customary cosmetic additives, antioxidants such as ascorbic acid or sodium sulfite, perfume oils, complex formers, wetting agents, emulsifiers, thickeners, hair care ingredients and others.

The form of application may be a solution, especially an aqueous or aqueous-alcoholic solution or preferably a cream, a gel or an emulsion. Its composition represents a mixture of the components with the ingredients customary for such application. As customary additives in solution, creams, emulsifiers or gels are for example solvents like water, low-aliphatic alcohols, as for example ethanol, propanol and isopropanol, or glycols such as glycerine and glycolether such as propyleneglycol, further wetting agents or emulsifiers from the class of anionic, cationic, amphoteric or non-ionogenic surface-active substances such as fatty alcohol sulfates, alkylsulfonates, alkylbenzene sulfonates, alkyltrimethylammonium salts, alkylbetaines, ethyoxylated fatty alcohols, ethoxylated nonylphenols, fatty acid alkanol amides, ethoxylated fatty acid esters, furthermore thickeners such as higher fatty alcohols, starch cellulose derivatives, vaseline, paraffin oil and finally also hair care ingredients such as lanolin derivatives, cholestrin, pantothenic acid and betaine. The aforenoted ingredients are used in quantities customary for such purposes, e.g. the wetting agents and emulsifiers in concentrations of 0.5 to 30% by weight, while the thickeners may be contained in the preparations in quantities of about 0.1 to 25% by weight.

Depending upon their composition, the hair coloring compositions according to the present invention may react slightly acid, neutral or alkaline. In particular, in the alkaline range they will be of a pH value between 8.0 and 11.5, adjustment being made preferably with ammonia. Use may, however, also be made or organic amines, for example monoethanolamine and triethanolamine, or also inorganic bases such as sodium hydroxide and potassium hydroxide.

In the method for oxidative dyeing of hair, the hair coloring compositions which contain a combination of developer substances known in hair dyeing with 1,3-diamino-4-(2',2',2'-trifluoroethoxy)-benzene of the formula I as coupler substance, and possibly additional known coupler substances, are mixed directly prior to its use with an oxidant and applied this mixture onto the hair. As oxidant for providing the hair dyeing, primarily hydrogen peroxide comes into consideration, for instance as 6% aqueous solution or, respectively, as its addition compounds with urea, melamine or sodium borate. The mixture is allowed to act upon the hair for about 10–45 minutes at 15°–50° C., preferably 30 minutes, after which the hair is rinsed with water and dried. If necessary, following the rinsing the hair is washed with a shampoo and eventually is rinsed with a weak organic acid, as for example citric acid or tartaric acid which acid is physiologically compatible.

The inventive new coupler substance 1,3-diamino-4-(2',2',2'-trifluoroethoxy)-benzene provides, in contrast to the known coupler substances, 2,4-diaminoanisole, 2,4-diaminophenetol and 2,4-diaminophenoxyethanol in combination with the developer substances 1,4-diaminobenzene and 2,5-diaminobenzyl alcohol mat blue tones without any red fraction. Moreover, these blue tones are stable for a much longer period and show only after a period of 2 months a slight graying without obtaining, however, a rust brown coloring.

A further advantage of the new coupler substance according to Formula I resides in the fact that the substance due to its low intensity of coloration in combination with p-aminophenol is usable in larger amounts in hair coloring compositions. Consequently, a concentration reduction of the coupler substance is prevented, which can occur through influences during storage. This effect is especially of relevance in hair coloring compositions for providing light mode tones. For example, for providing red fractions in light vogue tones, the intensively coloring developer substance-coupler substance combination 4-amino-phenol/2,4-diaminoanisole or 2,5-diaminotoluene/5-amino-2-methyl-phenol must be used in very low concentrations so far, thereby leading to non-reproducible colorings and to a non-uniform intensity of the coloring in dependence on different hair damages, for example between the hair tips and hair bases. In addition, a slight change of the concentration of an intensively coloring color component present in very small amounts can lead to a complete modification of the coloring shade, for example due to a too long storage period. Therefore, the hair coloring compositions according to the invention are especially suitable due to the content of the coupler substance of formula I for providing light vogue tones on previously blondined hair.

Finally, the black tones as provided with the new coupler substance of Formula I show very positive fastness as cannot be achieved for example with the combination 2-amino-4-(β-hydroxyethylamino)-anisole/m-phenylenediamine. The coupler substance according to the invention is further suitable in an extraordinary manner for the development of blue fractions requested in ash tones.

The novel features which are considered characteristic for the invention are set forth in particular in the appended claims. The invention itself, however, both as to its composition and its method of use, together with additional objects and advantages thereof, will be best understood from the following description of specific embodiments.

DESCRIPTION OF THE PREFERRED EMBODIMENTS

Example 1

Preparation of 1,3-diamino-4-(2',2',2'-trifluoroethoxy)-benzene

First step:

In a first reaction step, 1-chloro-2,4-dinitrobenzene (II) is reacted with 2,2,2-trifluoroethanolate to form 1,3-dinitro-4-(2',2',2'-trifluoroethoxy)-benzene (III) according to the following reaction:

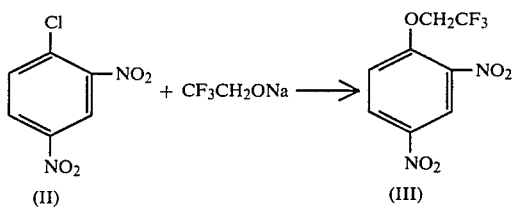

For obtaining this reaction, 4.0 g (0.17 mole) sodium is completely dissolved in 100 ml 2,2,2-trifluoroethanol. Thereafter, 21.5 g (0.11 mole) of finely powdered 1-chloro-2,4-dinitrobenzene is added to the solution. The mixture is then heated under reflux for 3 hours and the excessive trifluoroethanol is distilled off under normal pressure. The remaining oil is dissolved in 210 ml ethanol. Through addition of 170 ml water, the reaction product III is precipitated in a crystalline form. It is sucked off, washed with a water-ethanol mixture (1:1) and then dried over $CaCl_2$. The yield of 1,3-dinitro-4-(2',2',2'-trifluoroethoxy)-benzene is 27.0 g (0.1 mole 95% relative to the use 1-chloro-2,4-dinitrobenzene). The substance has a melting point of 76°–77° C.

| CHN-Analysis (%): | | C | H | N |
|---|---|---|---|---|
| ($C_8H_5F_3N_2O_5$) | calculated: | 36.10 | 1.89 | 10.52 |
| | found: | 36.15 | 1.92 | 10.55 |

Second step:

Through catalytic hydration of the nitro compound III in accordance with the following reaction, the desired 1,3-diamino-4-(2',2',2'-trifluoroethoxy)-benzene (I) is obtained.

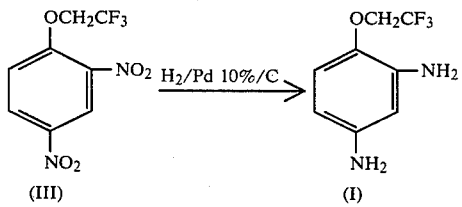

For obtaining this reaction, 6.3 g (0.024 mole) of 1,3-dinitro-4-(2',2',2'-trifluoroethoxy)-benzene is hydrated in 500 ml ethanol under addition of 0.45 g palladium on active carbon (10% palladium) at 30° C. The reception of hydrogen is terminated after approximately 1 hour. The catalyst is filtered off and the ethanol is distilled off. 4.56 g (0.022 mole, 93%) of crystalline solidified oil is obtained. The raw product is recrystallized for purification with 110 ml water under addition of a spatula tip of sodium sulfite and 0.1 g active carbon. The precipitated, colorless needles are sucked off, washed with a slight amount of water and finally dried. The yield of 1,3-diamino-4-(2',2',2'-trifluoroethoxy)-benzene is 1.80 g (0.0087 mole 37% relative to the used compound III). The substance has a melting point of 70°–71° C.

| CHN-Analysis (%): | | C | H | N |
|---|---|---|---|---|
| ($C_8H_9F_3N_2O$) | calculated: | 46.61 | 4.40 | 13.59 |
| | found: | 46.34 | 4.50 | 13.77 |

EXAMPLES FOR PROVIDING HAIR COLORING COMPOSITIONS

Example 2

Hair coloring composition in cream form

| | |
|---|---|
| 0.6 g | 1,3-diamino-4-(2',2',2'-trifluoroethoxy)-benzene |
| 1.7 g | resorcin |
| 2.0 g | 1,4-diaminobenzene |
| 0.3 g | sodium sulfite, water-free |
| 3.5 g | lauryl alcohol-diglycolethersulfate-sodium salt, 28% aqueous solution |
| 15.0 g | cetyl alcohol |
| 4.0 g | ammonia, 25% |
| 72.9 g | water |
| 100.0 g | |

50 g of the hair coloring composition is mixed directly prior to its use with 50 g hydrogen peroxide solution, 6%. The mixture is allowed to act upon blond natural hair for 30 minutes at 40° C. Afterwards, the coloring composition is rinsed, the hair is shampooed and dried. As a result, the hair has obtained a very intense mat black tone.

Example 3

Hair coloring solution

| | |
|---|---|
| 0.05 g | 1,3-diamino-4-(2',2',2'-trifluoroethoxy)-benzene |
| 0.05 g | resorcin |
| 0.10 g | m-aminophenol |
| 0.60 g | 2,5-diaminobenzylalcohol-dihydrochloride |
| 10.00 g | lauryl alcohol-diglycolethersulfate-sodium salt, 28% aqueous solution |
| 10.00 g | isopropanol |
| 0.30 g | sodium sulfite, water-free |
| 10.00 g | ammonia, 25% |
| 68.45 g | water |
| 100.00 g | |

50 g of this hair coloring composition are mixed directly prior to its use with 50 g hydrogen peroxide solution, 6%, and applied onto the bleached hair. After an application period of 30 minutes at 40° C., the hair has been dyed after rinsing, shampooing and drying to an ash blond coloring tone.

Example 4

Hair coloring composition in gel form

| | |
|---|---|
| 0.6 g | 1,3-diamino-4-(2',2',2'-trifluoroethoxy)-benzene |

-continued

| | |
|---|---|
| 0.5 g | p-aminophenol |
| 0.3 g | ascorbic acid |
| 15.0 g | oleic acid |
| 7.0 g | isopropanol |
| 9.0 g | ammonia, 25% |
| 67.6 g | water, completely desalted |
| 100.0 g | |

50 g of this hair coloring composition is mixed directly prior to its use with 50 g hydrogen peroxide solution, 6%, and is subsequently applied to the bleached hair for 30 minutes at a temperature of 40° C. After rinsing, shampooing and drying, the hair has been dyed to a light rose red tone.

All percentages stated in the present application are percentages by weight.

It will be understood that each of the elements described above, or two or more together, may also find a useful application in other types of cosmetic applications differing from the types described above.

While the invention has been illustrated and described as embodied in a composition for the oxidative coloration of hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. 1,3-diamino-4-(2',2',2'-trifluoroethoxy)-benzene of the formula I

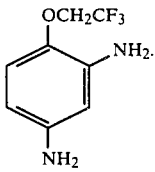

2. The acid additive salts of the compound of claim 1 obtained with inorganic or organic acids.

3. A composition for oxidative dyeing of hair, comprising a combination of
   (A) at least one developer substance customary in hair coloring; and
   (B) a coupler substance selected from the group consisting of 1,3-diamino-4-(2',2',2'-trifluoroethoxy)-benzene and the acid addition salts of 1,3-diamino-4-(2',2',2'-trifluoroethoxy)-benzene.

4. A composition as defined in claim 3, containing the component B in a concentration of 0.01 to 4.0 percent by weight.

5. A composition as defined in claim 4, containing the component B in a concentration of 0.02 to 2.0 percent by weight.

6. A composition as defined in claim 3, wherein the developer substance is selected from the group consisting of 1,4-diaminobenzene, 2,5-diaminotoluene, 2,5-diaminobenzyl alcohol, 4-aminophenol, 3-methyl-4-aminophenol, 2,5-diaminoanisole and tetraaminopyrimidine.

7. A composition as defined in claim 3; and further comprising a further coupler substance selected from the group consisting of 1-naphthol, 4-methoxy-1-naphthol, resorcin, 4-chlororesorcin, 4,6-dichlororesorcin, 2-methylresorcin, 2,4-dihydroxy-anisole, 2,4-dihydroxyphenoxyethanol, 4-hydroxy-1,2-methylenedioxybenzene, 4-amino-1,2-methylenedioxybenzene, 4-(β-hydroxyethylamino)-1,2-methylenedioxybenzene, m-aminophenol and 5-amino-2-methylphenol.

8. A composition as defined in claim 7, wherein the combination of developer substance-coupler substance is in an entire amount of 0.1 to 6.0% by weight.

9. A composition as defined in claim 8, wherein the entire amount of the combination is 0.5 to 3.0% by weight.

10. A composition as defined in claim 3; and further comprising a coloring component selected from the group consisting of 2-amino-5-methylphenol, 2-amino-6-methylphenol, 2-amino-5-ethoxyphenol and 2-propylamino-5-aminopyridine.

11. A composition as defined in claim 3; and further comprising a direct dyestuff selected from the group consisting of Diamond Fuchsin (C.I. 42 510), Leather Ruby HF (C.I. 42 520), 2-amino-4,6-dinitrophenol, 2-nitro-4-(β-hydroxyethylamino)-aniline, 2-amino-4-nitrophenol, Acid Brown 4 (C.I. 14 805), Acid Blue 135 (C.I. 13 385), Disperse Red 15 (C.I. 60 710), Disperse Violet 1 (C.I. 61 100), 1,4,5,8-tetraaminoanthraquinone and 1,4-diamino-anthraquinone.

12. A composition as defined in claim 3; and further comprising an antioxidant.

13. A composition as defined in claim 12, wherein the antioxidant is selected from the group consisting of ascorbic acid and sodium sulfite.

14. A composition as defined in claim 3, and further comprising a wetting agent.

15. A composition as defined in claim 3; and further comprising an emulsifier.

16. A composition as defined in claim 3; and further comprising a thickener.

* * * * *